United States Patent [19]

Aizawa et al.

[11] Patent Number: 4,997,639

[45] Date of Patent: Mar. 5, 1991

[54] METHOD FOR DETECTING CHOLESTEROL DEPOSITED IN BODIES OF MAMMALS

[75] Inventors: Katsuo Aizawa, Yokohama; Takayuki Asahara, Tanashi; Yukari Yasunaka, Kita, all of Japan

[73] Assignee: Nippon Petrochemicals Company, Limited, Tokyo, Japan

[21] Appl. No.: 441,303

[22] Filed: Nov. 27, 1989

[51] Int. Cl.$^5$ .................. A61K 49/00; G01N 31/00; G01N 33/48; G01N 37/10; G01N 31/40

[52] U.S. Cl. .................................. 424/9; 514/8; 514/410

[58] Field of Search .................. 514/8, 410; 540/145; 424/9

[56] References Cited

U.S. PATENT DOCUMENTS

| | | | |
|---|---|---|---|
| 4,656,186 | 4/1987 | Bommer et al. | 514/410 |
| 4,675,338 | 6/1987 | Bommer et al. | 514/410 |
| 4,693,885 | 9/1987 | Bommer et al. | 424/2 |

FOREIGN PATENT DOCUMENTS

| | | |
|---|---|---|
| 168831 | 1/1986 | European Pat. Off. . |
| 168832 | 1/1986 | European Pat. Off. . |
| 200218 | 11/1986 | European Pat. Off. . |
| 210351 | 2/1987 | European Pat. Off. . |
| 213272 | 3/1987 | European Pat. Off. . |

OTHER PUBLICATIONS

Neave, et al. *Neurosurgery*, vol. 23, pp. 307–12 (1988).

*Primary Examiner*—Stanley J. Friedman
*Assistant Examiner*—Theodore J. Criares
*Attorney, Agent, or Firm*—Scully, Scott, Murphy & Presser

[57] ABSTRACT

This invention relates to a novel method for detecting cholesterol which is deposited in the bodies of mammals, which method comprises the steps of administering to a host an effective amount of a photosensitizer of at least one member selected from the group consisting of tetrapyrrole carboxylic acids, corresponding di- or tetrahydropyrrole carboxylic acids, mono-, di- or polyamides of said tetrapyrrole carboxylic acids with amino-mono- or dicarboxylic acids, and salts of the above compounds; applying light of sufficient wavelength to the area of said mammal to be examined; and observing the fluorescence emitted from the area in which cholesterol is deposited.

9 Claims, 3 Drawing Sheets

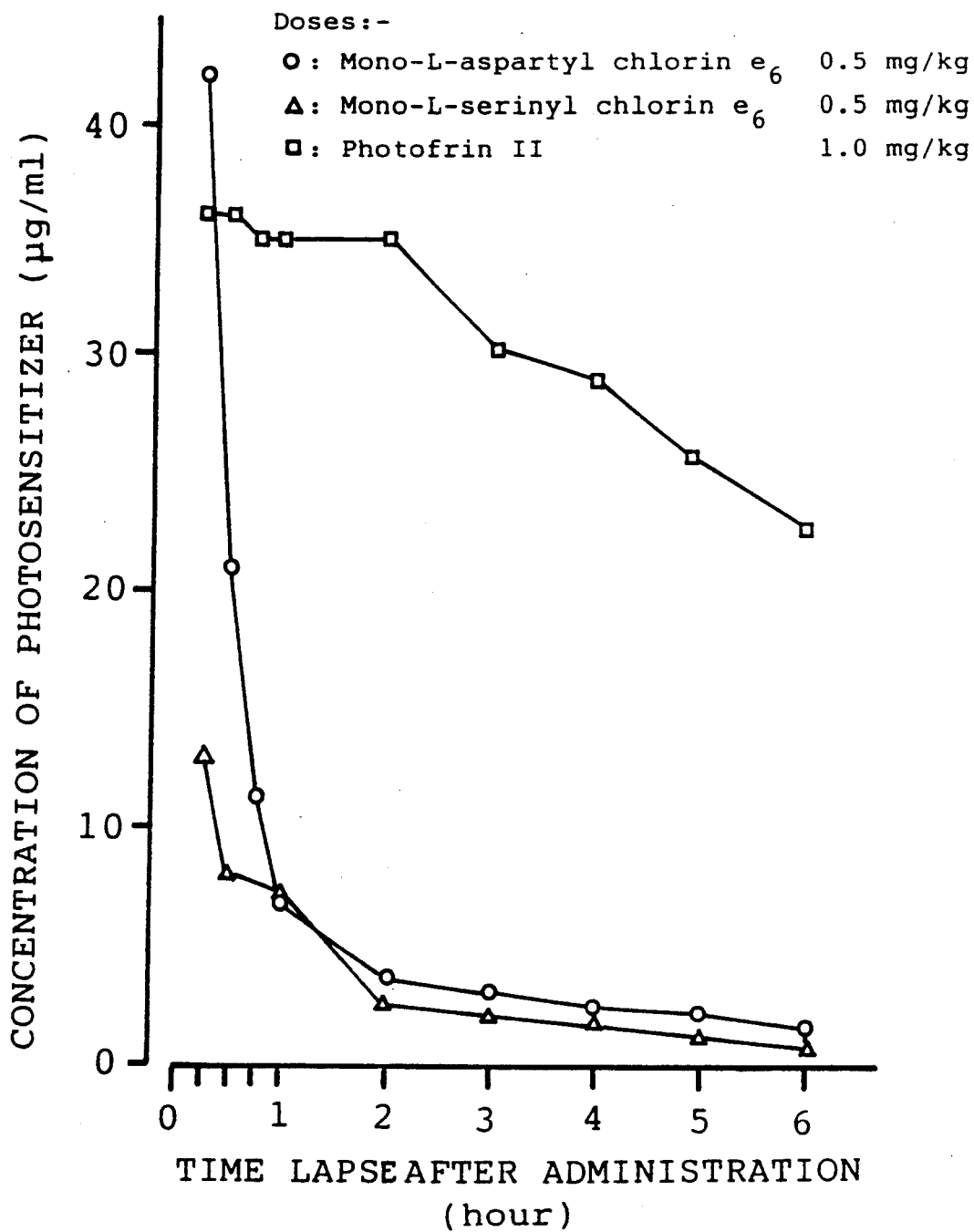

METHOD FOR DETECTING CHOLESTEROL DEPOSITED IN BODIES OF MAMMALS

BACKGROUND OF THE INVENTION (1) Field of the Invention

This invention relates to a method for detecting and measuring the amount of cholesterol which is deposited in the bodies of mammals.

(2) Description of the Prior Art

In the conventional art, there has been proposed no appropriate method for detecting directly or locally the cholesterol which is deposited in a living body, especially in the intima of artery of human body. For example, in the case of human body, it is difficult to determine the state of deposition of cholesterol by cytohystologic diagnosis in which an artery is cut open and the inside wall is subjected to macroscopic observation.

The state of deposition of cholesterol in the artery of human body was hitherto determined by injecting a contrast medium into an artery, taking an X-ray photograph and then observing the shadows on the obtained photograph. In another method, the determination of lipid (cholesterol) in serum was adopted. The result to this method, however, indicates the state of whole human body or considerably large part of the body, and the state of any specific part cannot be determined.

In the determination of cholesterol in blood, cholesterol is oxidized by an enzyme and generated peroxide and dye-precursor are subjected to oxidation-coupling in the presence of an enzyme, and then the quantity of developed dye is determined by absorptiometric analysis. It is difficult to determine the cholesterol deposited in a living body, especially in arteries, by means of the method utilizing chemical reaction like this.

It is said that arteriosclerosis, especially atherosclerosis of human as well as other mammals is caused by the deposition in the intima of cholesterol contained in blood. Thus, for the purpose of preventing or treating the atherosclerosis, a medicine having an effect to reduce the cholesterol value in the serum of human is administered.

The substance which causes atherosclerosis in human body by depositing in intima is a kind of of lipids which are produced in living bodies. At least the vertebrate animals, especially mammals, are concerned, such chemical compounds are known generally as cholesterol because the fundamental skeletal structures of them are the same.

There is hitherto known a method for the diagnosis of arteriosclerosis by administering a hematoporphyrin derivative to rabbits. A typical hematoporphyrin is exemplified by PHOTOFRIN II (trademark supplied by Photofrin Medical Inc.) This example is desribed in the following reference:

V. Neave et al., NEUROSURGERY, vol. 23, pp 307-312

However, it was found by the inventors of the present invention that the generation of fluorescence is weak when the foregoing Photofrin II is used for the method of the present invention. In the case that the generated fluorescence is weak, the determination of cholesterol is difficult because the cholesterol is determined by measuring the generated fluorescence in the method of the present invention.

Incidentally, the compounds themselves used in the method of the present invention are already known as diagnostic and therapeutic agents for cancer which are described in European Laid-Open Patent Publication Nos. 168831, published Jan. 22, 1986, equivalent to U.S. Pat. No. 4,693,885, issued Sept. 15, 1987;--; 168832, published Jan. 22, 1986, equivalent to U.S. Pat. No. 4,675,338, issued June 23, 1987;--; 200218, published Nov. 5, 1986, equivalent to U.S. Pat. No. 4,656,186, issued Apr. 7, 1987;--; 210351, published Feb. 4, 1987 and 213272, published Mar. 11, 1987. It should be noted that the field of art in the present invention is of course different from the field of art in the diagnosis and therapy of cancer.

BRIEF SUMMARY OF THE INVENTION

It is therefore the primary object of the present invention to provide a novel method for detecting and measuring the amount of cholesterol which is deposited in the bodies of mammals.

Another object of the present invention is to provide a method for detecting cholesterol by which method the detection can be carried out sensitively at high precision without difficult operation.

A further object of the present invention is to provide a method for detecting cholesterol by which method the detection can be carried out rapidly at low cost.

In accordance with the present invention, the method for detecting the cholesterol in the bodies of animals is characterized in that:

administering to a host an effective amount of at least one photosensitizer selected from the group consisting of tetrapyrrole carboxylic acid having at least one carboxylic acid group represented by the following general formula, and corresponding di- or tetrahydrotetrapyrrole carboxylic acids, and mono-, di- and polyamides of said tetrapyrrole carboxylic acids with amino-mono- or dicarboxylic acids, and their salts;

applying light of sufficient wavelength to the area of the mammal to be examined; and observing the fluorescence emitted from the area in which cholesterol is deposited.

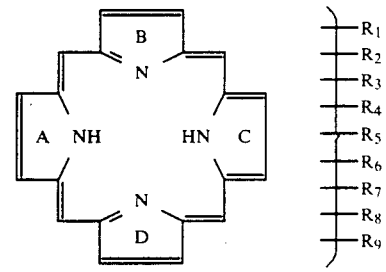

BRIEF DESCRIPTION OF DRAWINGS

These and other objects and features of the invention will become more apparent from the following detailed description and examples with reference to the accompanying drawings, in which:

FIG. 3 is a graphic chart also showing the change of concentration of photosensitizer with the passage of time in atherosclerotic rabbits.

DETAILED DESCRIPTION OF THE INVENTION

Figure 1:
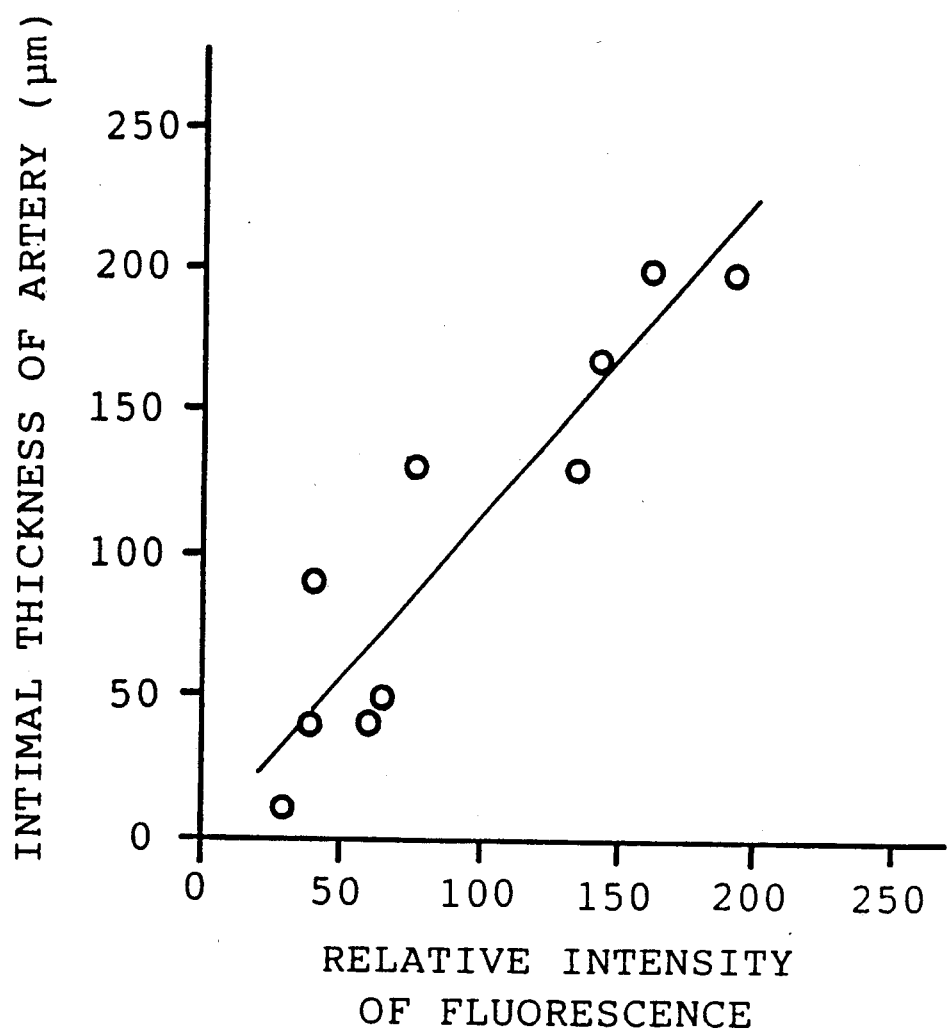
FIG. 1 is a graphic chart showing the relation between the intimal thickness of artery and the relative intensity of emitted fluorescence.

The cholesterol is a kind of lipids exists in most of animals, especially in vertebrate animals At least the substances of this kind existing in the bodies of mammals have a common fundamental skeletal structure, so that they are included in the category of the cholesterol. They exist in a free state or in the forms of esters with higher fatty acid. Furthermore, there are dihydro-type and saturated type cholesterols. This cholesterol is also called as cholesterin. The term "cholesterol" referred to in the present invention designate these compounds. Especially, the cholesterol in the present invention indicates a substance which is deposited in the intima of artery and, in the case of human, which causes atherosclerosis.

All of the compounds used in the method of the present invention are fluorescent compounds (photosensitizers). Tetrapyrrole carboxylic acid of the foregoing general formula is firstly named. The tetrapyrrole carboxylic acid has at least one and preferably three carboxylic acid groups. Also included in the compounds of the present invention are dior tetrahydrotetrapyrrole carboxylic acid which corresponds to the above tetrapyrrole. Furthermore, pharmaceutically acceptable salts of the carboxyl groups of these carboxylic acids such as salts of alkali metals, alkaline earth metals, ammonium and amines are included.

Furthermore, the compounds used in the present invention are mono-, di- or polyamides of amino monocarboxylic acid with the above tetrapyrrole carboxylic acids. Another usable group of compounds are pharmaceutically acceptable salts of the carboxyl groups of these mono-, di or polyamides such as salts of alkali metals, alkaline earth metals, ammonium and amines.

The above amino monocarboxylic acids which forms mono-, di- or polyamide by connecting to the above tetrapyrrole carboxylic acid by way of polypeptide bonds are exemplified by serine, glycine, α-aminoalanine, β-aminoalanine, ε-amino-n-caproic acid, piperidine-2-carboxylic acid, piperidine-6-carboxylic acid, pyrrole-2-carboxylic acid, piperidine-2-propionic acid, pyrrole-5-acetic acid, and similar such acids The preferred amino acids are the naturally occurring α-amino monocarboxylic acids such as serine, alanine and glycine, which are readily available and up to the present, have provided the best results.

Exemplar amino dicarboxylic acids are α-aminosuccinic acid (aspartic acid) α-aminoglutaric acid (glutamic acid), β-aminoglutaric acid, β-aminosebacic acid, 2,6-piperidine dicarboxylic acid, 2,5-pyrrole dicarboxylic acid, 2-carboxypyrrole-5-acetic acid, 2-carboxypiperidine 6-propionic acid, α-aminoadipic acid, and α-aminoazelaic acid. The preferred amino dicarboxylic acids are the naturally occurring α-amino dicarboxylic acids such as aspartic acid and glutamic acid.

The tetrapyrrole carboxylic acids used in the method of the present invention are represented by the following structural formula.

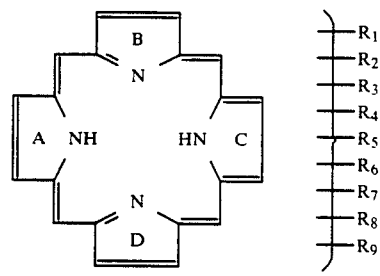

wherein
$R_1$ is methyl,

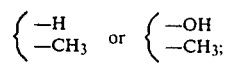

$R_2$ is H, vinyl, ethyl,

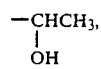

acetyl,

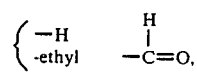

$CH_2CH_2CO_2H$ or $=CHCHO$;
$R_3$ is methyl,

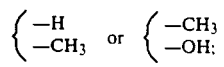

$R_4$ is H, vinyl, ethyl,

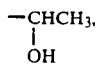

$CH_2CH_2CO_2H$,
$=CHCHO$ or

$R_5$ is methyl;
$R_6$ is H, $CH_2CH_2CO_2H$, $CH_2CH_2CO_2R$ or $CO_2H$;
$R_7$ is $CH_2CH_2CO_2H$, $CH_2CH_2CO_2R$ or

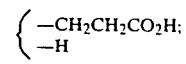

$R_8$ is methyl or

$R_9$ is H, COOH, $CH_2COOH$ or methyl; provided that when $R_1$, $R_2$, $R_3$, $R_4$, $R_7$ and $R_8$ represents two substituents or are divalent and attached to the same carbon, the respective pyrrole ring to which attached is a dihydropyrrole;

R is lower alkyl or benzyl;

$R_6$ and $R_9$, taken together are

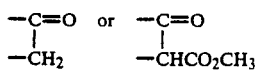

with the proviso that at least one of $R_1$–$R_9$ is a free carboxyl group.

The preferred tetrapyrrole carboxylic acids are those wherein at least three carboxylic acid groups are present in the tetrapyrrole, preferably asymmetrically attached to the porphyrin ring system, e.g., the carboxylic acid groups are present on the rings A and B side of the molecule or on the rings D and C side of the molecule.

The particularly preferred tetrapyrrole is represented by the following general formula:

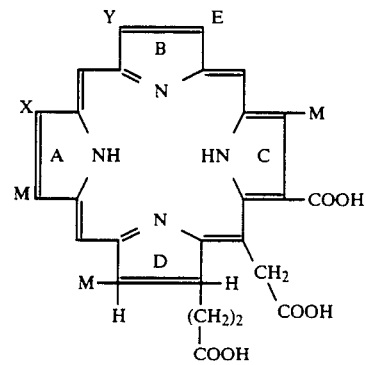

wherein;

X is H, vinyl, ethyl, acetyl or formyl;

Y is methyl or formyl;

M is methyl; and

E is ethyl

Typical compounds of the tetrapyrrole classes are illustrated in Table 1 in which the numbered positions of the tetrapyrrole ring structure are used to designate the position of the indicated substituent. The absence of double bonds in the ring system is designated under "dihydro" with each set of numbers (ring position) indicating the absence of a double bond between the designated positions.

TABLE 1

| Porphyrin | A 1 | A 2 | B 6 | B 7 | C 11 | C 12 | 14 | D 16 | D 17 | Dihydro |
|---|---|---|---|---|---|---|---|---|---|---|
| Coproporphyrin III | Me | Pr | Me | Pr | Me | Pr | H | Pr | Me | — |
| Deuteroporphyrin IX | Me | H | Me | H | Me | Pr | H | Pr | Me | — |
| Hematoporphyrin IX | Me | Me—CH—OH | Me | Me—CH—OH | Me | Pr | H | Pr | Me | — |
| Protoporphyrin IX | Me | V | Me | V | Me | Pr | H | Pr | Me | — |
| Photoprotoporphyrin IX (one of two isomers shown) | Me | V | {—Me, —OH} | =CHCHO | Me | Pr | H | Pr | Me | 6,7 |
| Mesoporphyrin IX | Me | Et | Me | Et | Me | Pr | H | Pr | Me | — |
| Transmesochlorin IX | {Me, H} | {Et, H} | Me | Et | Me | Pr | H | Pr | Me | 1,2 |
| Transmesochlorin IX | Me | Et | {H, Me} | {H, Et} | Me | Pr | H | Pr | Me | 6,7 |
| Chlorin $e_4$ | Me | V | Me | Et | Me | $CO_2H$ | Me | {H, Pr} | {H, Me} | 16,17 |
| Chlorin $e_6$ | Me | V | Me | Et | Me | $CO_2H$ | Ac | {H, Pr} | {H, Me} | 16,17 |
| Mesochlorin $e_4$ | Me | Et | Me | Et | Me | $CO_2H$ | Me | {H, Pr} | {H, Me} | 16,17 |
| Isochlorin $e_4$ | Me | V | Me | Et | Me | H | Ac | {H, Pr} | {H, Me} | 16,17 |

TABLE 1-continued

| Porphyrin | Ring Position A 1 | A 2 | B 6 | B 7 | C 11 | C 12 | C 14 | D 16 | D 17 | Dihydro |
|---|---|---|---|---|---|---|---|---|---|---|
| Mesoisochlorin e₄ | Me | Et | Me | Et | Me | H | Ac | {H, Pr} | {H, Me} | 16,17 |
| Mesochlorin e₆ | Me | Et | Me | Et | Me | CO₂H | Ac | {H, Pr} | {H, Me} | 16,17 |
| Bacteriochlorin e₆ | Me | ACL | {H, Me} | {H, Et} | Me | CO₂H | Ac | {H, Pr} | {H, Me} | 6, 7 16,17 |
| Bacteriochlorin e₄ | Me | ACL | {H, Me} | {H, Et} | Me | CO₂H | Me | {H, Pr} | {H, Me} | 6, 7 16,17 |
| Bacterioisochlorin e₄ | Me | ACL | {H, Me} | {H, Et} | Me | H | Ac | {H, Pr} | {H, Me} | 6, 7 16,17 |
| 2-Desvinylchlorin e₆ (or Deuterochlorin e₆) | Me | H | Me | Et | Me | CO₂H | Ac | {H, Pr} | {H, Me} | 16,17 |
| 2-Acetylchlorin e₆ | Me | ACL | Me | Et | Me | CO₂H | Ac | {H, Pr} | {H, Me} | 16,17 |
| 2-Formylchlorin e₆ | Me | CHO | Me | Et | Me | CO₂H | Ac | {H, Pr} | {H, Me} | 16,17 |

Notes:
Me: —CH₃ (Methyl group)
Et: —CH₂CH₃ (Ethyl group)
Pr: —CH₂CH₂COOH (Propionic acid group)
Ac: —CH₂COOH (Acetic acid group)
V: —CH=CH₂ (Vinyl group)
ACL: CH₃—CO— (Acetyl group)

In the following, exemplar amides used in the present invention will be described.

The following compounds are exemplified as the mono-, di- or polyamides of amino monocarboxylic acids. Chlorin Derivatives:
(D,L)-Serinyl-trans-mesochlorin IX
Glycyl-trans-mesochlorin IX
α-(D,L)-Alanyl-trans-mesochlorin IX
β-Alanyl-trans-mesochlorin IX
ε-Amino-n-caproyl-mesochlorin IX
(D,L)-Serinyl chlorin e₆
(D,L)-Serinyl mesochlorin e₆
Glycyl chlorin e₆
Glycyl mesochlorin e₆
α-(D,L)-Alanyl chlorin e₆
α-(D,L)-Alanyl mesochlorin e₆
β-Alanyl chlorin e₆
β-Alanyl mesochlorin e₆
ε-Amino-n-caproyl chlorin e₆
ε-Amino-n-caproyl mesochlorin e₆
(D,L)-Serinyl chlorin e₄
(D,L)-Serinyl mesochlorin e₄
(D,L)-Serinyl isochlorin e₄
(D,L)-Serinyl mesoisochlorin e₄
Glycyl chlorin e₄
Glycyl mesochlorin e₄
Glycyl isochlorin e₄
Glycyl mesoisochlorin e₄
α-(D,L)-Alanyl chlorin e₄
α-(D,L)-Alanyl mesochlorin e₄
α-(D,L)-Alanyl isochlorin e₄
α-(D,L)-Alanyl mesoisochlorin e₄
β-Alanyl chlorin e₄
β-Alanyl mesochlorin e₄
β-Alanyl isochlorin e₄
β-Alanyl mesoisochlorin e₄
ε-Amino-n-caproyl chlorin e₄
ε-Amino-n-caproyl mesochlorin e₄
ε-Amino-n-caproyl isochlorin e₄
ε-Amino-n-caproyl mesoisochlorin e₄
(D,L)-Serinyl pyropheophorbide a
Glycyl pyropheophorbide a
α-(D,L)-Alanyl pyropheophorbide a
β-Alanyl pyropheophorbide a
ε-Amino-n-caproyl pyropheophorbide a
(D,L)-Serinyl pheophorbide a
Glycyl pheophorbide a
α-(D,L)-Alanyl pheophorbide a
β-Alanyl pheophorbide a
ε-Amino-n-caproyl pheophorbide a
(D,L)-Serinyl photoprotoporphyrin IX
Glycyl photoprotoporphyrin IX α-(D,L)-Alanyl-photoprotoporphyrin IX
β-Alanyl photoprotoporphyrin IX
ε-Amino-n-caproyl photoprotoporphyrin IX
Threoninyl chlorin $e_6$
Tyrosyl chlorin $e_6$
Valyl chlorin $e_6$
Leucyl chlorin $e_6$
Isoleucyl chlorin $e_6$
Prolyl chlorin $e_6$
Methionyl chlorin $e_6$
Histidyl chlorin $e_6$
Arginyl chlorin $e_6$
Lysyl chlorin $e_6$
Glutaminyl chlorin $e_6$
4-Hydroxyprolyl chlorin $e_6$
5-Hydroxylysyl chlorin $e_6$
ε-amino-n-caproyl chlorin $e_6$
γ-aminobutanoyl chlorin $e_6$
3-Methyl histidyl chlorin $e_6$
Alanyl-2-acetyl chlorin $e_6$
Valyl-2-acetyl chlorin $e_6$
Leucyl-2-acetyl chlorin $e_6$
Isoleucyl-2-acetyl chlorin $e_6$
Prolyl-2-acetyl chlorin $e_6$
Methionyl-2-acetyl chlorin $e_6$
Glycyl-2-acetyl chlorin $e_6$
Serinyl-2-acetyl chlorin $e_6$
Threoninyl-2-acetyl chlorin $e_6$
Cysteinyl-2-acetyl chlorin $e_6$
Tyrosyl-2-acetyl chlorin $e_6$
Asparginyl-2-acetyl chlorin $e_6$
Lysyl-2-acetyl chlorin $e_6$
Arginyl-2-acetyl chlorin $e_6$
Histidyl-2-acetyl chlorin $e_6$
Glutaminyl-2-acetyl chlorin $e_6$
4-Hydroxyprolyl-2-acetyl chlorin $e_6$
5-Hydroxylysyl-2-acetyl chlorin $e_6$
ε-Amino-n-caproyl-2-acetyl chlorin $e_6$
γ-Aminobutanoyl-2-acetyl chlorin $e_6$
3-Methyl histidyl-2-acetyl chlorin $e_6$
β-Alanyl-2-acetyl chlorin $e_6$
Alanyl-2-formyl chlorin $e_6$
Valyl-2-formyl chlorin $e_6$
Leucyl-2-formyl chlorin $e_6$
Isoleucyl-2-formyl chlorin $e_6$
Prolyl-2-formyl chlorin $e_6$
Methionyl-2-formyl chlorin $e_6$
Glycyl-2-formyl chlorin $e_6$
Serinyl-2-formyl chlorin $e_6$
Threoninyl-2-formyl chlorin $e_6$
Cysteinyl-2-formyl chlorin $e_6$
Tyrosyl-2-formyl chlorin $e_6$
Asparginyl-2-formyl chlorin $e_6$
Lysyl-2-formyl chlorin $e_6$
Arginyl-2-formyl chlorin $e_6$
Histidyl-2-formyl chlorin $e_6$
Glutaminyl-2-formyl chlorin $e_6$
4-Hydroxyprolyl-2-formyl chlorin $e_6$
5-Hydroxylysyl-2-formyl chlorin $e_6$
ε-Amino-n-caproyl-2-formyl chlorin $e_6$
γ-Aminobutanoyl-2-formyl chlorin $e_6$ 3-Methyl histidyl-2-formyl chlorin $e_6$
β-Alanyl-2-formyl chlorin $e_6$
Alanyl deuterochlorin $e_6$
Valyl deuterochlorin $e_6$
Leucyl deuterochlorin $e_6$
Isoleucyl deuterochlorin $e_6$
Prolyl deuterochlorin $e_6$
Methionyl deuterochlorin $e_6$
Glycyl deuterochlorin $e_6$
Serinyl deuterochlorin $e_6$
Threoninyl deuterochlorin $e_6$
Cysteinyl deuterochlorin $e_6$
Tyrosyl deuterochlorin $e_6$
Asparginyl deuterochlorin $e_6$
Lysyl deuterochlorin $e_6$
Arginyl deuterochlorin $e_6$
Histidyl deuterochlorin $e_6$
Glutaminyl deuterochlorin $e_6$
4-Hydroxyprolyl deuterochlorin $e_6$
5-Hydroxylysyl deuterochlorin $e_6$
ε-Amino-n-caproyl deuterochlorin $e_6$
γ-Aminobutanoyl deuterochlorin $e_6$
3-Methyl histidyl deuterochlorin $e_6$
β-Alanyl deuterochlorin $e_6$
Valyl mesochlorin $e_6$
Leucyl mesochlorin $e_6$
Isoleucyl mesochlorin $e_6$
Prolyl mesochlorin $e_6$
Methionyl mesochlorin $e_6$
Serinyl mesochlorin $e_6$
Threoninyl mesochlorin $e_6$
Cysteinyl mesochlorin $e_6$
Tyrosyl mesochlorin $e_6$
Asparginyl mesochlorin $e_6$
Lysyl mesochlorin $e_6$
Arginyl mesochlorin $e_6$
Histidyl mesochlorin $e_6$
Glutaminyl mesochlorin $e_6$
4-Hydroxyprolyl mesochlorin $e_{66}$
5-Hydroxylysyl mesochlorin $e_6$
γ-Aminobutanoyl mesochlorin $e_6$
3-Methyl histidyl mesochlorin $e_6$ Porphyrin Derivatives (D,L)-Serinyl mesoporphyrin IX
Glycyl mesoporphyrin IX
α-(D,L)-Alanyl mesoporphyrin IX
β-Alanyl mesoporphyrin IX
ε-Amino-n-caproyl mesoporphyrin IX
(D,L)-Serinyl protoporphyrin IX
Glycyl protoporphyrin IX
α-(D,L)-Alanyl protoporphyrin IX
β-Alanyl protoporphyrin IX
ε-Amino-n-caproyl protoporphyrin IX
(D,L)-Serinyl deuteroporphyrin IX
Glycyl deuteroporphyrin IX
α-(D,L)-Alanyl deuteroporphyrin IX
β-Alanyl deuteroporphyrin IX
ε-Amino-n-caproyl deuteroporphyrin IX
(D,L)-Serinyl coproporphyrin III
Glycyl coproporphyrin III
α-(D,L)-Alanyl coproporphyrin III β-Alanyl coproporphyrin III
ε-Amino-n-caproyl coproporphyrin III
(D,L)-Serinyl hematoporphyrin IX
Glycyl hematoporphyrin IX
α-(D,L)-Alanyl hematoporphyrin IX
β-Alanyl hematoporphyrin IX
ε-Amino-n-caproyl hematoporphyrin IX

Bacteriochlorin Derivatives (D,L)-Serinyl bacteriochlorin $e_4$
Glycyl bacteriochlorin $e_4$
α-(D,L)-Alanyl bacteriochlorin $e_4$
β-Alanyl bacteriochlorin $e_4$
ε-Amino-n-caproyl bacteriochlorin $e_4$
(D,L)-Serinyl bacterioisochlorin $e_4$
Glycyl bacterioisochlorin $e_4$
α-(D,L)-Alanyl bacterioisochlorin $e_4$
β-Alanyl bacterioisochlorin $e_4$
ε-Amino-n-caproyl bacterioisochlorin $e_4$
(D,L)-Serinyl bacteriochlorin $e_6$
Glycyl bacteriochlorin $e_6$
α-(D,L)-Alanyl bacteriochlorin $e_6$
β-Alanyl bacteriochlorin $e_6$
ε-Amino-n-caproyl bacteriochlorin $e_6$
(D,L)-Serinyl pyrobacteriopheophorbide a
Glycyl pyrobacteriopheophorbide a
α-(D,L)-Alanyl pyrobacteriopheophorbide a
β-Alanyl pyrobacteriopheophorbide a
ε-Amino-n-caproyl pyrobacteriopheophorbide a
(D,L)-Serinyl bacteriopheophorbide a
Glycyl bacteriopheophorbide a
α-(D,L)-Alanyl bacteriopheophorbide a
β-Alanyl bacteriopheophorbide a
ε-Amino-n-caproyl bacteriopheophorbide a Di- or polyamides of amino monocarboxylic acids are further exemplified.

Chlorin Derivatives

Di-(D,L)-serinyl-trans-mesochlorin IX
Di-glycyl-trans-mesochlorin IX
Di-α-(D,L)-alanyl-trans-mesochlorin IX
Di-β-alanyl-trans-mesochlorin IX
Di-ε-amino-n-caproyl-mesochlorin IX
Di, tri-(D,L)-serinyl chlorin $e_6$
Di, tri-(D,L)-serinyl mesochlorin $e_6$
Di, tri-glycyl chlorin $e_6$
Di, tri-glycyl mesochlorin $e_6$
Di, tri-α-(D,L)-alanyl chlorin $e_6$
Di, tri-α-(D,L)-alanyl mesochlorin $e_6$
Di, tri-β-alanyl chlorin $e_6$
Di, tri-β-alanyl mesochlorin $e_6$
Di, tri-ε-amino-n-caproyl chlorin $e_6$
Di, tri-ε-amino-n-caproyl mesochlorin $e_6$
Di-(D,L)-serinyl chlorin $e_4$
Di-(D,L)-serinyl mesochlorin $e_4$
Di-(D,L)-serinyl isochlorin $e_4$
Di-(D,L)-serinyl mesoisochlorin $e_4$
Di-glycyl chlorin $e_4$
Di-glycyl mesochlorin $e_4$
Di-glycyl isochlorin $e_4$
Di-glycyl mesoisochlorin $e_4$
Di-α-(D,L)-alanyl chlorin $e_4$
Di-α-(D,L)-alanyl mesochlorin $e_4$
Di-α-(D,L)-alanyl isochlorin $e_4$
Di-α-(D,L)-alanyl mesoisochlorin $e_4$
Di-β-alanyl chlorin $e_4$
Di-β-alanyl mesochlorin $e_4$
Di-β-alanyl isochlorin $e_4$
Di-β-alanyl mesoisochlorin $e_4$
Di-ε-amino-n-caproyl chlorin $e_4$
Di-ε-amino-n-caproyl mesochlorin $e_4$
Di-ε-amino-n-caproyl isochlorin $e_4$
Di-ε-amino-n-caproyl mesoisochlorin $e_4$
Di-(D,L)-serinyl photoprotoporphyrin IX
Di-glycyl photoprotoporphyrin IX
Di-α-(D,L)-alanyl-photoprotoporphyrin IX
Di-β-alanyl photoprotoporphyrin IX
Di-ε-amino-n-caproyl photoprotoporphyrin IX

Porphyrin Derivatives

Di-(D,L)-serinyl mesoporphyrin IX
Di-glycyl mesoporphyrin IX
Di-α-(D,L)-alanyl mesoporphyrin IX
Di-β-alanyl mesoporphyrin IX
Di-ε-amino-n-caproyl mesoporphyrin IX
Di-(D,L)-serinyl protoporphyrin IX
Di-glycyl protoporphyrin IX
Di-α-(D,L)-alanyl protoporphyrin IX
Di-β-alanyl protoporphyrin IX
Di-ε-amino-n-caproyl protoporphyrin IX
Di-(D,L)-serinyl deuteroporphyrin IX
Di-glycyl deuteroporphyrin IX
Di-α-(D,L)-alanyl deuteroporphyrin IX
Di-β-alanyl deuteroporphyrin IX
Di-ε-amino-n-caproyl deuteroporphyrin IX
Di, tri, tetra-(D,L)-serinyl coproporphyrin III
Di, tri, tetra-glycyl coproporphyrin III
Di, tri, tetra-α-(D,L)-alanyl coproporphyrin III
Di, tri, tetra-β-alanyl coproporphyrin III
Di, tri, tetra-ε-amino-n-caproyl coproporphyrin III
Di-(D,L)-serinyl hematoporphyrin IX
Di-glycyl hematoporphyrin IX
Di-α-(D,L)-alanyl hematoporphyrin IX
Di-β-alanyl hematoporphyrin IX
Di-ε-amino-n-caproyl hematoporphyrin IX

Bacteriochlorin Derivatives

Di-(D,L)-serinyl bacteriochlorin $e_4$
Di-glycyl bacteriochlorin $e_4$
Di-α-(D,L)-alanyl bacteriochlorin $e_4$
Di-β-alanyl bacteriochlorin $e_4$
Di-ε-amino-n-caproyl bacteriochlorin $e_4$
Di-(D,L)-serinyl bacterioisochlorin $e_4$
Di-glycyl bacterioisochlorin $e_4$
Di-α-(D,L)-alanyl bacterioisochlorin $e_4$
Di-β-alanyl bacterioisochlorin $e_4$
Di-ε-amino-n-caproyl bacterioisochlorin $e_4$
Di-(D,L)-serinyl bacteriochlorin $e_6$
Di-glycyl bacteriochlorin $e_6$
Di-α-(D,L)-alanyl bacteriochlorin $e_6$
Di-β-alanyl bacteriochlorin $e_6$
Di-ε-amino-n-caproyl bacteriochlorin $e_6$ Similarly, by utilizing other amino acids, the following peptides can be employed, however, they do not limit the present invention.

Di-threoninyl trans-mesochlorin IX
Di, tri-threoninyl chlorin $e_6$

Di, tri-threoninyl mesochlorin e₆
Di-threoninyl chlorin e₄
Di-threoninyl mesochlorin e₄
Di-threoninyl isochlorin e₄
Di-threoninyl mesoisochlorin e₄
Di-threoninyl photoprotoporphyrin IX
Di-threoninyl mesoporphyrin IX
Di-threoninyl protoporphyrin IX
Di-threoninyl deuteroporphyrin IX
Di, tri, tetra-threoninyl coproporphyrin III
Di-threoninyl hematoporphyrin IX
Di-threoninyl bacteriochlorin e₄
Di-threoninyl bacterioisochlorin e₄
Di, tri-threoninyl bacteriochlorin e₆
Di-cysteinyl trans-mesochlorin IX
Di, tri-cysteinyl chlorin e₆
Di, tri-cysteinyl mesochlorin e₆
Di-cysteinyl chlorin e₄
Di-cysteinyl mesochlorin e₄
Di-cysteinyl isochlorin e₄
Di-cysteinyl mesoisochlorin e₄
Di-cysteinyl photoprotoporphyrin IX
Di-cysteinyl mesoporphyrin IX
Di-cysteinyl protoporphyrin IX
Di-cysteinyl deuteroporphyrin IX
Di, tri, tetra-cysteinyl coproporphyrin III
Di-cysteinyl hematoporphyrin IX
Di-cysteinyl bacteriochlorin e₄
Di-cysteinyl bacterioisochlorin e₄
Di, tri-cysteinyl bacteriochlorin e₆
Di-tyrosyl trans-mesochlorin IX
Di, tri-tyrosyl chlorin e₆
Di, tri-tyrosyl mesochlorin e₆
Di-tyrosyl chlorin e₄
Di-tyrosyl mesochlorin e₄
Di-tyrosyl isochlorin e₄
Di-tyrosyl mesoisochlorin e₄
Di-tyrosyl photoprotoporphyrin IX
Di-tyrosyl mesoporphyrin IX
Di-tyrosyl protoporphyrin IX
Di-tyrosyl deuteroporphyrin IX
Di, tri, tetra-tyrosyl coproporphyrin III
Di-tyrosyl hematoporphyrin IX
Di-tyrosyl bacteriochlorin e₄
Di-tyrosyl bacterioisochlorin e₄
Di, tri-tyrosyl bacteriochlorin e₆
Di-valyl trans-mesochlorin IX
Di, tri-valyl chlorin e₆
Di, tri-valyl mesochlorin e₆
Di-valyl chlorin e₄
Di-valyl mesochlorin e₄
Di-valyl isochlorin e₄
Di-valyl mesoisochlorin e₄
Di-valyl photoprotoporphyrin IX
Di-valyl mesoporphyrin IX
Di-valyl protoporphyrin IX
Di-valyl deuteroporphyrin IX
Di, tri, tetra-valyl coproporphyrin III
Di-valyl hematoporphyrin IX
Di-valyl bacteriochlorin e₄
Di-valyl bacterioisochlorin e₄
Di, tri-valyl bacteriochlorin e₆
Di-leucyl trans-mesochlorin IX
Di, tri-leucyl chlorin e₆
Di, tri-leucyl mesochlorin e₆
Di-leucyl chlorin e₄
Di-leucyl mesochlorin e₄
Di-leucyl isochlorin e₄
Di-leucyl mesoisochlorin e₄
Di-leucyl photoprotoporphyrin IX
Di-leucyl mesoporphyrin IX
Di-leucyl protoporphyrin IX
Di-leucyl deuteroporphyrin IX
Di, tri, tetra-leucyl coproporphyrin III
Di-leucyl hematoporphyrin IX
Di-leucyl bacteriochlorin e₄
Di-leucyl bacterioisochlorin e₄
Di, tri-leucyl bacteriochlorin e₆
Di-isoleucyl trans-mesochlorin IX
Di, tri-isoleucyl chlorin e₆
Di, tri-isoleucyl mesochlorin e₆
Di-isoleucyl chlorin e₄
Di-isoleucyl mesochlorin e₄
Di-isoleucyl isochlorin e₄
Di-isoleucyl mesoisochlorin e₄
Di-isoleucyl photoprotoporphyrin IX
Di-isoleucyl mesoporphyrin IX
Di-isoleucyl protoporphyrin IX
Di-isoleucyl deuteroporphyrin IX
Di, tri, tetra-isoleucyl coproporphyrin III
Di-isoleucyl hematoporphyrin IX
Di-isoleucyl bacteriochlorin e₄
Di-isoleucyl bacterioisochlorin e₄
Di, tri-isoleucyl bacteriochlorin e₆
Di-prolyl trans-mesochlorin IX
Di, tri-prolyl chlorin e₆
Di, tri-prolyl mesochlorin e₆
Di-prolyl chlorin e₄
Di-prolyl mesochlorin e₄
Di-prolyl isochlorin e₄
Di-prolyl mesoisochlorin e₄
Di-prolyl photoprotoporphyrin IX
Di-prolyl mesoporphyrin IX
Di-prolyl protoporphyrin IX
Di-prolyl deuteroporphyrin IX
Di, tri, tetra-prolyl coproporphyrin III
Di-prolyl hematoporphyrin IX
Di-prolyl bacteriochlorin e₄
Di-prolyl bacterioisochlorin e₄
Di, tri-prolyl bacteriochlorin e₆
Di-phenylalanyl trans-mesochlorin IX
Di, tri-phenylalanyl chlorin e₆
Di, tri-phenylalanyl mesochlorin e₆
Di-phenylalanyl chlorin e₄
Di-phenylalanyl mesochlorin e₄
Di-phenylalanyl isochlorin e₄
Di-phenylalanyl mesoisochlorin e₄
Di-phenylalanyl photoprotoporphyrin IX
Di-phenylalanyl mesoporphyrin IX
Di-phenylalanyl protoporphyrin IX
Di-phenylalanyl deuteroporphyrin IX
Di, tri, tetra-phenylalanyl coproporphyrin III
Di-phenylalanyl hematoporphyrin IX
Di-phenylalanyl bacteriochlorin e₄
Di-phenylalanyl bacterioisochlorin e₄
Di-phenylalanyl bacteriochlorin e₆

Di-tryptophyl trans-mesochlorin IX
Di, tri-tryptophyl chlorin $e_6$
Di, tri-tryptophyl mesochlorin $e_6$
Di-tryptophyl chlorin $e_4$
Di-tryptophyl mesochlorin $e_4$
Di-tryptophyl isochlorin $e_4$
Di-tryptophyl mesoisochlorin $e_4$
Di-tryptophyl photoprotoporphyrin IX
Di-tryptophyl mesoporphyrin IX
Di-tryptophyl protoporphyrin IX
Di-tryptophyl deuteroporphyrin IX
Di, tri, tetra-tryptophyl coproporphyrin III
Di-tryptophyl hematoporphyrin IX
Di-tryptophyl bacteriochlorin $e_4$
Di-tryptophyl bacterioisochlorin $e_4$
Di, tri-tryptophyl bacteriochlorin $e_6$
Di-methionyl trans-mesochlorin IX
Di, tri-methionyl chlorin $e_6$
Di, tri-methionyl mesochlorin $e_6$
Di-methionyl chlorin $e_4$
Di-methionyl mesochlorin $e_4$
Di-methionyl isochlorin $e_4$
Di-methionyl mesoisochlorin $e_4$
Di-methionyl photoprotoporphyrin IX
Di-methionyl mesoporphyrin IX
Di-methionyl protoporphyrin IX
Di-methionyl deuteroporphyrin IX
Di, tri, tetra-methionyl coproporphyrin III
Di-methionyl hematoporphyrin IX
Di-methionyl bacteriochlorin $e_4$
Di-methionyl bacterioisochlorin $e_4$
Di, tri-methionyl bacteriochlorin $e_6$
Di-histidyl trans-mesochlorin IX
Di, tri-histidyl chlorin $e_6$
Di, tri-histidyl mesochlorin $e_6$
Di-histidyl chlorin $e_4$
Di-histidyl mesochlorin $e_4$
Di-histidyl isochlorin $e_4$
Di-histidyl mesoisochlorin $e_4$
Di-histidyl photoprotoporphyrin IX
Di-histidyl mesoporphyrin IX
Di-histidyl protoporphyrin IX
Di-histidyl deuteroporphyrin IX
Di, tri, tetra-histidyl coproporphyrin III
Di-histidyl hematoporphyrin IX
Di-histidyl bacteriochlorin $e_4$
Di-histidyl bacterioisochlorin $e_4$
Di, tri-histidyl bacteriochlorin $e_6$
Di-arginyl trans-mesochlorin IX
Di, tri-arginyl chlorin $e_6$
Di, tri-arginyl mesochlorin $e_6$
Di-arginyl chlorin $e_4$
Di-arginyl mesochlorin $e_4$
Di-arginyl isochlorin $e_4$
Di-arginyl mesoisochlorin $e_4$
Di-arginyl photoprotoporphyrin IX
Di-arginyl mesoporphyrin IX
Di-arginyl protoporphyrin IX
Di-arginyl deuteroporphyrin IX
Di, tri, tetra-arginyl coproporphyrin III
Di-arginyl hematoporphyrin IX
Di-arginyl bacteriochlorin $e_4$
Di-arginyl bacterioisochlorin $e_4$
Di, tri-arginyl bacteriochlorin $e_6$
Di-lysyl trans-mesochlorin IX
Di, tri-lysyl chlorin $e_6$
Di, tri-lysyl mesochlorin $e_6$
Di-lysyl chlorin $e_4$
Di-lysyl mesochlorin $e_4$
Di-lysyl isochlorin $e_4$
Di-lysyl mesoisochlorin $e_4$
Di-lysyl photoprotoporphyrin IX
Di-lysyl mesoporphyrin IX
Di-lysyl protoporphyrin IX
Di-lysyl deuteroporphyrin IX
Di, tri, tetra-lysyl coproporphyrin III
Di-lysyl hematoporphyrin IX
Di-lysyl bacteriochlorin $e_4$
Di-lysyl bacterioisochlorin $e_4$
Di, tri-lysyl bacteriochlorin $e_6$
Di-glutaminyl trans-mesochlorin IX
Di, tri-glutaminyl chlorin $e_6$
Di, tri-glutaminyl mesochlorin $e_6$
Di-glutaminyl chlorin $e_4$
Di-glutaminyl mesochlorin $e_4$
Di-glutaminyl isochlorin $e_4$
Di-glutaminyl mesoisochlorin $e_4$
Di-glutaminyl photoprotoporphyrin IX
Di-glutaminyl mesoporphyrin IX
Di-glutaminyl protoporphyrin IX
Di-glutaminyl deuteroporphyrin IX
Di, tri, tetra-glutaminyl coproporphyrin III
Di-glutaminyl hematoporphyrin IX
Di-glutaminyl bacteriochlorin $e_4$
Di-glutaminyl bacterioisochlorin $e_4$
Di, tri-glutaminyl bacteriochlorin $e_6$
Di-asparginyl trans-mesochlorin IX
Di, tri-asparginyl chlorin $e_6$
Di, tri-asparginyl mesochlorin $e_6$
Di-asparginyl chlorin $e_4$
Di-asparginyl mesochlorin $e_4$
Di-asparginyl isochlorin $e_4$
Di-asparginyl mesoisochlorin $e_4$
Di-asparginyl photoprotoporphyrin IX
Di-asparginyl mesoporphyrin IX
Di-asparginyl protoporphyrin IX
Di-asparginyl deuteroporphyrin IX
Di, tri, tetra-asparginyl coproporphyrin III
Di-asparginyl hematoporphyrin IX
Di-asparginyl bacteriochlorin $e_4$
Di-asparginyl bacterioisochlorin $e_4$
Di, tri-asparginyl bacteriochlorin $e_6$ In the following, mono-, di- or polyamides of amino dicarboxylic acids are exemplified.

Chlorin Derivatives

Mono and diaspartyl trans-mesochlorin IX
Mono and diglutamyl trans-mesochlorin IX
Mono, di and triaspartyl chlorin $e_6$
Mono, di and triaspartyl mesochlorin $e_6$
Mono, di and triglutamyl chlorin $e_6$
Mono, di and triglutamyl mesochlorin $e_6$
Mono and diaspartyl chlorin $e_4$
Mono and diaspartyl mesochlorin $e_4$
Mono and diaspartyl isochlorin $e_4$
Mono and diaspartyl mesoisochlorin $e_4$ Mono and diglutamyl chlorin e$_4$
Mono and diglutamyl mesochlorin e$_4$
Mono and diglutamyl isochlorin e$_4$
Mono and diglutamyl mesoisochlorin e$_4$
Monoaspartyl pyropheophorbide a
Monoglutamyl pyropheophorbide a
Monoaspartyl pheophorbide a
Monoglutamyl pheophorbide a
Mono and diaspartyl photoprotoporphyrin IX
Mono and diglutamyl photoprotoporphyrin IX
Mono and di-L-alpha-aminoadipyl trans-mesochlorin IX

Porphyrin Derivatives

Mono and diaspartyl mesoporphyrin IX
Mono and diglutamyl mesoporphyrin IX
Mono and diaspartyl protoporphyrin IX
Mono and diglutamyl protoporphyrin IX
Mono and diaspartyl deuteroporphyrin IX
Mono and diglutamyl deuteroporphyrin IX
Mono, di, tri and tetraaspartyl coproporphyrin III (isomer mixture)
Mono, di, tri and tetraglutamyl coproporphyrin III
Mono and diaspartyl hematoporphyrin IX
Mono and diglutamyl hematoporphyrin IX

Bacteriochlorin Derivatives

Mono and diaspartyl bacteriochlorin e$_4$
Mono and diglutamyl bacteriochlorin e$_4$
Mono and diaspartyl bacterioisochlorin e$_4$
Mono and diglutamyl bacterioisochlorin e$_4$
Mono, di and triaspartyl bacteriochlorin e$_6$
Mono, di and triglutamyl bacteriochlorin e$_6$
Monoaspartyl pyrobacteriopheophorbide a
Monoglutamyl pyrobacteriopheophorbide a Especially preferable compounds in the present invention are dihydro or tetrahydro type amides of tetrapyrrole carboxylic acids with amino acids.

Several methods for preparing the compounds of the present invention are known in the conventional art. For example, they can be prepared by the methods as described in the foregoing European Laid-Open Patent Publication Nos. 168831, 168832, 200218, 210351 and 213272.

Method for Measurement

The practical method for measuring the deposited cholesterol in living bodies will be described in detail in the following examples. The outline of the measurement method is described in the first place.

A compound of the present invention which is dissolved in an appropriate aqueous solution such as a phosphate buffered saline solution (pH 7.4), is administered by a proper method to the living body of a host to be examined. The aqueous solution may be an aqueous dispersion containing a suitable dispersing agent. When the cholesterol deposited in the intima of artery is to be examined, it is preferable that the aqueous solution is administered by a direct method such as injection. Meanwhile, the oral, intramuscular and hypodermic administration are also possible. In any case, the solution of the compound of the present invention may also contain the following materials: a binder such as gum tragacanth; an excipient such as dicalcium phosphate; a disintegrating agent such as corn starch; a lubricant such as magnesium stearate; a sweetening agent such as sucrose; a preservative such as paraben; a dye; a flavoring such as cherry flavor; a solvent or dispersion medium such as water, ethanol or glycol; an antiseptic; and an isotonic agent such as sugar and sodium chloride. The quantity of administration is determined on the degree of accumulation to cholesterol, however, it is generally selected within the range of 0.01 to 100 mg/kg (weight of living body).

The host which is a living body to receive the administration, is a mammal which has cholesterol within its body. Even though the method of the present invention can be applied to almost all other animals as well as mammals, especially to vertebrates, there is not considered any practical application to other animals.

Even though the reason has not been clear, the compounds of the present invention are specifically and selectively accumulated in the area in which cholesterol is deposited. Accordingly, after the passage of an appropriate time, for example, after several minutes to several tens of hours from the intravenous administration of a compound, a light ray of 360 to 760 nm, e.g. 405 nm, in wavelength is applied to an aorta in which cholesterol is deposited. The light source for the irradiation in diagnosis is not limited, however, a laser beam is generally used because a strong light ray within a desired wavelength range can be applied selectively. In addition, the intensity of light can also be selected properly. Relatively weak irradiation is sufficient for the measurement because the fluorescence emitted by the compound of the present invention is intense, however, the intensity of irradiation can be generally selected from the range of 10 to 1000 mW/cm$^2$.

The compound of the present invention which is accumulated in a area containing deposited cholesterol, emits fluorescence when it is applied with light rays.

The amount of deposited cholesterol is determined by measuring the intensity of fluorescence in the range around the specific wavelength of emitted fluorescence. Because emitted fluorescence is characteristic of each substance, it is necessary that the specific wavelength must be confirmed by measuring it in advance. The specific wave-length is, for example, 670 nm for mono-L-aspartyl chlorin e$_6$ and mono-L-serinyl chlorin e$_6$ were used in the examples of the present invention. The emitted fluorescence is measured (detected) by means of an appropriate fluoro-spectrometric analyzer. In the measurement of deposited cholesterol in an interior part of living body such as in an intima, it is desirable that fluorescence is introduced and measured using a glass fiber bundle.

In the area in which any deposition of cholesterol is not detected by angioscopic observation or histological test with incision of artery, even when the compound of the present invention is administered to the host and a light ray of the above specific wavelength is applied to the relevant part, any substantial emission of fluorescence of the above wavelength is not detected generally.

Incidentally, the specific wavelength of fluorescence which is emitted from the compound of the present invention that is caught in the deposited cholesterol, is shifted by about 10 nm as compared with the same compound in a phosphate buffered saline solution From this fact, it is considered that the compound of the present invention is not simply and physically caught within cholesterol but it is connected to the cholesterol by some interconnection mechanism. When the wavelength is shifted, the change in the intensity of fluorescence is also caused to occur usually. However, in the case of the compounds of the present invention, the intensity of fluorescence is not weakened but rather strengthened. Accordingly, the compounds of the present invention is most suitable for the photodynamic-diagnosis (PDD).

In comparison with the use of conventional HPD and Photofrin II, it has been observed that the compounds of the present invention generate more intense fluorescence with an administration in the same quantity in similar part of cholesterol deposition.

The degree of deposition of cholesterol can be also confirmed totally by histological diagnosis, endoscopic observation and measurement of the degree of thickening of the intima of artery as well as the measurement of the emission of fluorescence.

The compound of the present invention is apparently innocuous with the dose for the above-described diagnostic purpose. For example, it is apparent from the fact that any test animals were not killed owing to the compound of the present invention in experiments using doses up to the extent of 20 mg/kg.

EXAMPLE

Preparation of Mono-L-Aspartyl Chlorin $e_6$

Test compound of mono-L-aspartyl chlorin $e_6$ was prepared according to the method described in the foregoing European Laid-Open Patent Publication No. 168832.

150 mg of chlorin $e_6$ and 250 mg of L-aspartic acid di-t-butyl ester hydrochloride were dissolved in 20 ml of dimethyl formamide. There was made a total of 3–100 mg additions of N,N'-dicyclohexyl-carbodiimide at one hour intervals. After 4 hours, the reaction mixture was diluted with 300 ml ether, washed twice with 200 ml $H_2O$ then extracted with 40 ml 1 M KOH. The KOH solution was allowed to hydrolyze overnight, then heated to 70° C. for 10 minutes.

The pH of the solution was adjusted to 7, then any residual ether was removed by flash evaporation. The solution was then applied to a reverse phase (C-18 silica) column (1.5 cm × 30 cm). The product was purified by a stepwise elution of methanol/0.01 M pH 6.85 $KPO_4$ buffer. Eluted with 5% methanol until unwanted polar pigments were removed. Monoaspartyl chlorin $e_6$ was eluted off with 6–8% methanol, and unreacted chlorin $e_6$ was removed with 25% methanol.

The product was precipitated at pH 3 after flash evaporating briefly to remove methanol, then washed at the centrifuge 3 times with dilute acetic acid.

The product was dried under vacuum. Yield of mono-L-aspartyl chlorin $e_6$ was 50 mg.

Preparation of Mono-L-Serinyl Chlorin $e_6$

Test compound of mono-L-serinyl chlorin $e_6$ was prepared according to the method described in the foregoing European Laid-Open Patent Publication No. 213272.

100 mg of chlorin $e_6$ (free acid form) and 35 mg of 1-ethyl-3-(3-dimethylaminopropyl) carbodiimide hydrochloride were dissolved in 2 ml of N,N'-dimethyl formamide. After 5 minutes, 125 mg of L-serine benzyl ester hydrochloride was added, stirred vigorously until solution was complete, then allowed to stand at room temperature for 2 hours. At this time 0.5 ml of glacial acetic acid was added then 30 ml of methanol and 12 ml of $H_2O$.

The solution was applied to a C-18 reverse phase column (14 × 2 cm). The column was washed with $H_2O$ (100 ml) then 4 ml of 1 N $NH_4OH$, then with $H_2O$ again (50 ml). Eluted product with MeOH/$H_2O$. Fractions eluted from the column with 30% to 80% MeOH contained product as well as carbodiimide activated chlorin as determined by TLC on C-18 reverse phase plate with solvent 70% MeOH/30% buffer (0.1 M sodium phosphate, pH 6.85) V/V.

These fractions were pooled and enough 3 N NaOH was added to make the solution 0.1 N NaOH. After 1 hour, the hydrolysis was complete as determined by TLC in the above system. Removed the methanol by rotary evaporation and adjusted the pH of the solution to 7.5 with HCl. The chlorin solution was then reapplied to the same reverse phase column, washed with water, and eluted with MeOH/water using a stepwise gradient from 10 to 50% methanol. The fractions containing pure mono-L-serinyl chlorin as determined by TLC ($R_f$ slightly greater than the unsubstituted chlorin) were pooled, the methanol removed by rotary evaporation, and the product dried as the trisodium salt by lyophylization.

These test compounds were used by dissolving them in phosphate buffered saline solution (pH 7.4). As a comparative compound, Photofrin II (trademark, made by Photofrin Medical Inc.) was used as it stands. Photofrin II was obtained in a concentration of 2.5 mg/ml as an aqueous solution.

Animal Test

Normal Japanese white rabbits (supplied by Japan Laboratory Animals Inc.) and another group of the same white rabbits which took artificial arteriosclerosis (hereinafter referred to as "atherosclerotic rabbits") were used for experiments.

By inserting a Fogarty catheter into the inguinal region of a rabbit, the abdominal aorta and thoracic aorta were scrubbed and peeled. After that, the rabbits were bred with a feed containing 2% cholesterol and 10% peanut oil for 8 to 12 weeks, thereby obtaining atherosclerotic rabbits.

Test Apparatus

The apparatus for this experiment includes an angioscopic catheter (made by Sumitomo Electric Industries, Ltd.), an excimer dye laser (made by Hamamatsu Photonics K.K.) for exciting photosensitizer and an angioscopic fluorescence analyzer system. This spectrum analyzer can observe the image of the angioscope. The angioscopic catheter is provided with an image fiber, a light fiber, a fluorescence introducing fiber and multifunctional working channel The measurement was carried out by inserting the angioscopic catheter into an artery. The excimer dye laser generates pulse laser of 405 nm in wavelength, 10 nsec. in pulse width, 0.1 mJ/pulse in the output of tip of introducing fiber and 3.75 Hz in frequency. This pulse laser was introduced into a quartz fiber bundle of 300 micrometer in core diameter and it is then passed to the multifunctional working channel and further led into artery.

By the way, when both the angioscopic image and fluorescence spectrum were measured simultaneously, a phosphate buffered saline solution (pH 7.4) was injected through the multifunctional working channel in order to remove the obstructive blood.

1) Observation of Intima of Artery by Means of Angioscopic Fluorescence Analyzer System Each photosensitizer was administered to atherosclerotic rabbits intravenously according to the following conditions in Table 2.

TABLE 2

| Compound | Dose | After Injection |
|---|---|---|
| Photofrin II | 5 mg/kg | 24 hours |
| Mono-L-aspartyl chlorin $e_6$ | 5 mg/kg | 24 hours |
| Mono-L-aspartyl chlorin $e_6$ | 0.5 mg/kg | 6 hours |
| Mono-L-serinyl chlorin $e_6$ | 0.5 mg/kg | 6 hours |

An angioscope was introduced into the abdominal aorta at 6 hours and 24 hours after the administration and the fluorescence spectrum of the photosensitizer in the atheroma area and normal area in artery was measured by the fluorescence analyzing system. At the same time, the endoarterial image in the angioscope was observed.

A similar experiment was carried out with regard to normal rabbits as controls Furthermore, similar experiment was also carried out with regard to atherosclerotic rabbits which were not administered with the photosensitizer.

2) Measurement of Accumulation of Photosensitizer

Relative to the Degree of Arteriosclerosis A dose 0.5 mg/kg of mono-L-aspartyl chlorin $e_6$ was administered to an atherosclerotic rabbit, and at 6 hours after the administration, the abdominal aorta was excised and it was cut open. The fluorescence spectrum of the photosensitizer was measured by scanning the intima of the artery. Furthermore, the intimal thickness was measured with regard to the section of the same area, thereby investigating the relation between the accumulation of photosensitizer and the intimal thickness.

RESULT OF EXPERIMENT

1) Observation of Intima of Artery by Means of Angioscopic Fluorescence Analyzer System (a) The angioscope was introduced into the abdominal aorta of the atherosclerotic rabbits which was administered with none of the photosensitizer and the intima of artery was then observed When both normal areas and atheroma areas were excited with 405 nm beam no fluorescence was detected in the wavelength range of 600 to 700 nm.

(b) The foregoing doses of photosensitizer were administered to normal rabbits At 6 hours and 24 hours after the administration, the fluorescence spectrum of the substance in the intima was not observed at all.

(c) Doses of 0.5 mg/kg or 5 mg/kg of each photosensitizer were administered to atherosclerotic rabbits and fluorescence spectra in intimae were observed at 6 hours and 24 hours after the administration.

In the atheroma areas, the fluorescence spectrum having a specific peak at 670 nm was observed in mono-L-aspartyl chlorin $e_6$ in mono-L-serinyl chlorin $e_6$ and twin-peak fluorescence spectrum having specific peaks at 630 and 690 nm was observed in Photofrin II. Relative intensities of fluorescence of photosensitizer were calculated from the areal integral of fluorescence spectra in the range of 600 to 700 nm.

The relative intensities of the photosensitizer were 4.25 in Photofrin II and 18.30 in mono-L-aspartyl chlorin $e_6$ in the cases of 5 mg/kg doses measured at 24 hours after the administration; and 17.48 in mono-L-aspartyl chlorin $e_6$ and 16.30 in mono-L-serinyl chlorin $e_6$ in the cases of 0.5 mg/kg doses measured at 6 hours after the administration.

In normal areas, the relative intensities were 1.35 in Photofrin II and 0.88 in mono-L-aspartyl chlorin $e_6$ in the cases of 5 mg/kg doses measured at 24 hours after the administration; and 1.68 in mono-L-aspartyl chlorin $e_6$ and 1.75 in mono-L-serinyl chlorin $e_6$ in the cases of 0.5 mg/kg doses measured at 6 hours after the administration.

Furthermore, with regard to each photosensitizer, the ratio of maximum value (atheroma area) to minimum value (normal area) was calculated. The ratios were 3.1 in Photofrin II and 20.8 in mono-L-aspartyl chlorin $e_6$ in the cases of 5 mg/kg doses measured at 24 hours after the administration, showing a high selectivity to atheroma area; and 10.4 in mono-L-aspartyl chlorin $e_6$ and 9.3 in mono-L-serinyl chlorin $e_6$ in the cases of 0.5 mg/kg doses measured at 6 hours after the administration, also showing a good selectivity to atheroma area. These results are summarized in the following Table 3.

TABLE 3

| Photo-sensitizer | Dose (mg/kg) | Hours After Injection | Atheroma Rabbit Max. | Atheroma Rabbit Min. | Atheroma Rabbit Ratio* | Normal Rabbit |
|---|---|---|---|---|---|---|
| Photofrin II | 5.0 | 24 | 4.25 | 1.35 | 3.1 | 0.0 |
| Mono-L-aspartyl chlorin $e_6$ | 5.0 | 24 | 18.30 | 0.88 | 20.8 | 0.0 |
| Mono-L-aspartyl chlorin $e_6$ | 0.5 | 6 | 17.48 | 1.68 | 10.4 | 0.0 |
| Mono-L-serinyl chlorin $e_6$ | 0.5 | 6 | 16.30 | 1.75 | 9.3 | 0.0 |

Note: *Ratio = Max./Min.

2) Measurement of Accumulation of Photosensitizer Relative to the Degree of Arteriosclerosis A dose of 0.5 mg/kg of mono-L-aspartyl chlorin $e_6$ was administered to an atherosclerotic rabbit, and at 6 hours after the administration, the abdominal aorta was excised and it was cut open. The fluorescence spectrum of the photosensitizer was measured by scanning the intima of the artery and the intimal thickness was measured with regard to the section of the same part, thereby examining the relation between the accumulation of photosensitizer and the intimal thickness.

The quantities of photosensitizer taken into intimae were varied in proportion to the thickening of intimae. The coefficient of correlation was 0.92 and the coefficient of determination was 0.84 between the intensity of fluorescence and the thickening of intima in mono-L-aspartyl chlorin $e_6$, which showed a close correlation between them. These results are shown in the following Table 4 and FIG. 1.

TABLE 4

| Tested Point | Relative intensity of Fluorescence | Intimal Thickness (mm) |
|---|---|---|
| Point 1 | 39 | 90 |
| Point 2 | 159 | 200 |
| Point 3 | 191 | 200 |
| Point 4 | 76 | 130 |
| Point 5 | 31 | 10 |
| Point 6 | 135 | 130 |
| Point 7 | 41 | 40 |

TABLE 4-continued

| Tested Point | Relative intensity of Fluorescence | Intimal Thickness (mm) |
|---|---|---|
| Point 8 | 65 | 50 |
| Point 9 | 61 | 40 |
| Point 10 | 142 | 170 |

According to the above test results, the following facts were clarified.

(a) In the atheroma areas, a fluorescence spectrum having a specific peak at 670 nm was observed in mono-L-aspartyl chlorin $e_6$ and in mono-L-serinyl chlorin $e_6$. Meanwhile a twin-peak fluorescence spectrum having specific peaks at 630 and 690 nm was observed in Photofrin II.

(b) In the areas which are considered to be normal, the fluorescence spectra of photosensitizer were scarcely detected in the range of 600 to 700 nm.

(c) According to the comparison in the ratios of the quantities of photosensitizer accumulated in atheroma areas to those in normal areas, the hystological selectivities (tendency to be accumulated in atheroma areas) of mono-L-aspartyl chlorin $e_6$ and mono-L-serinyl chlorin $e_6$ were superior to that of Photofrin II.

(d) The quantity of accumulation of mono-L-aspartyl chlorin $e_6$ in the tissue of artery was proportional to the thickening of intima and their correlation was significant.

(e) With regard to the state of distribution of mono-L-aspartyl chlorin $e_6$ in the tissue of artery, red fluorescence was observed in atheroma areas in intimae showing the existence of mono-L-aspartyl chlorin $e_6$, however, the fluorescence was not found in the normal tissues of elastic fiber, media and adventitia.

From the above results, it was made possible to examine the occurrence of arteriosclerosis in the intima of artery by using photosensitizer which are selective to atheroma area and an angioscopic fluorescence analyzer system.

Changes in Concentrations of Photosensitizer in Serum with the Passage of Time

Each of the following photosensitizer was administered to atherosclerotic rabbits intravenously.

| Mono-L-aspartyl chlorin $e_6$ | 0.5 mg/kg dose |
|---|---|
| Mono-L-serinyl chlorin $e_6$ | 0.5 mg/kg dose |
| Photofrin II | 1 mg/kg dose |

In order to measure the concentrations of the photosensitizer in serum, blood was collected before the administration and at 2.5, 15, 30, 45 and 60 minutes and 2, 3, 4, 5, 6 and 24 hours after the administration. Serum was separated by a centrifuge of 3000 rpm for 10 minutes and it was subjected to the measurement of fluorescence spectra. The concentration of each photosensitizer was calculated by a calibration curve which was prepared by the following procedure.

As controls, normal rabbits were also administered with the following doses, respectively.

| Mono-L-aspartyl chlorin $e_6$ | 0.5 mg/kg dose |
|---|---|
| Mono-L-serinyl chlorin $e_6$ | 0.5 mg/kg dose |
| Photofrin II | 0.5 mg/kg dose |

Before the administration, blood was taken from each rabbit and serum was separated, to which was added one of the photosensitizer and mixed together to prepare respective mixtures of $1 \times 10^{-6}$ to $1 \times 10^{-8}$ mol/l in final concentration. The thus prepared mixtures were left to stand for 1 hour in a dark room and the spectra of photosensitizer were measured to make calibration curves.

Result of Experiment

3) Changes in Concentrations of Photosensitizer in Serum with the Passage of Time Normal rabbits were administered with 0.5 mg/kg of any one of mono-L-aspartyl chlorin $e_6$, mono-L-serinyl chlorin $e_6$ and Photofrin II and, the concentrations of photosensitizer were measured with the passage of time. The concentrations in serum of both the mono-L-aspartyl chlorin $e_6$ and mono-L-serinyl chlorin $e_6$ were reduced rapidly. At 3 hours after the administration, the concentration of mono-L-asparyl chlorin $e_6$ was 2.6 $\mu$g/ml and mono-L-serinyl chlorin $e_6$, 0.3 $\mu$g/ml. The concentration of Photofrin II in serum was about 10 $\mu$g/ml and was not so changed during 2.5 minutes to 3 hours after the administration and the concentration was reduced gradually thereafter.

At 24 hours after the administration, the concentration in serum of remaining mono-L-aspartyl chlorin $e_6$ was as low as 0.2 $\mu$g/ml and mono-L-serinyl chlorin $e_6$, 0.0 $\mu$g/ml, while the concentration of remaining Photofrin II was 2 $\mu$g/ml.

Atherosclerotic rabbits were administered with 0.5 mg/kg of mono-L-aspartyl chlorin $e_6$, 0.5 mg/kg of and 1 mg/kg of mono-L-serinyl chlorin $e_6$ and 1 mg/kg of Photofrin II and concentrations in serum were measured in the like manner as the above.

The concentration of mono-L-aspartyl chlorin $e_6$ was 42.4 $\mu$g/ml at 15 minutes after the administration, and then the concentration was rapidly reduced to 21.2 $\mu$g/ml after 30 minutes, 6.6 $\mu$g/ml after 1 hour and 1.6 $\mu$g/ml after 6 hours.

The concentration of mono-L-serinyl chlorin $e_6$ was 12.9 $\mu$g/ml at 15 minutes after the administration, and then the concentration was also rapidly reduced to 7.9 $\mu$g/ml after 30 minutes, 6.1 $\mu$g/ml after 1 hour and 0.8 $\mu$g/ml after 6 hours.

The concentration of Photofrin II was not so changed as about 35 $\mu$g/ml during 15 minutes to 2 hours after the administration and 21.5 $\mu$g/ml after 6 hours. Setting The concentration at 15 minutes after the administration as 100%, the percentage in the concentration at 6 hours after the administration were as follows: 3.8% in mono-L-aspartyl chlorin $e_6$ and 6.2% in mono-L-serinyl chlorin $e_6$ and 61.4% in Photofrin II.

Therefore, Photofrin II remained considerably in serum, however, mono-L-aspartyl chlorin $e_6$ and mono-L-serinyl chlorin $e_6$ were rapidly excreted from serum.

Figure 2:
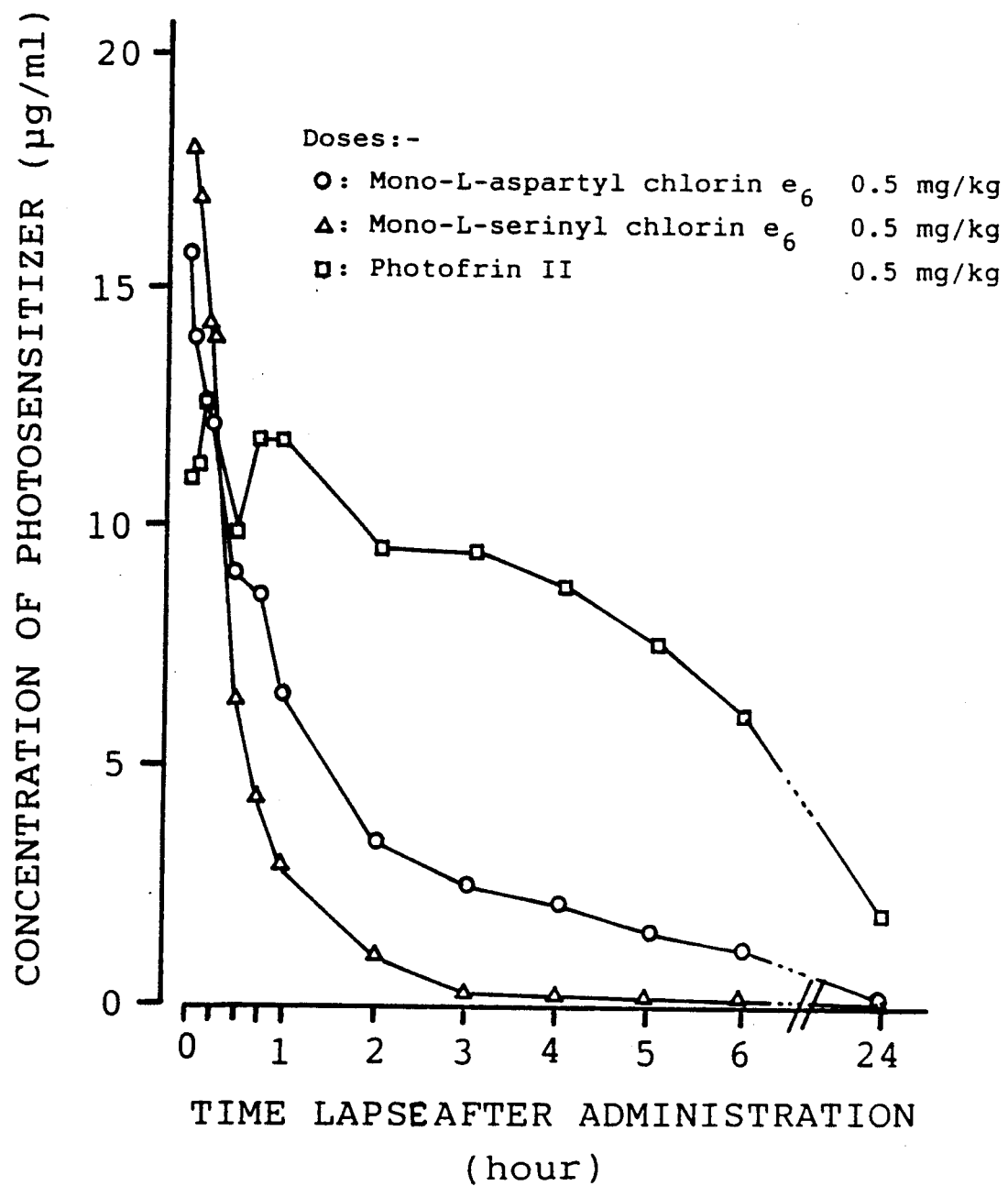
FIG. 2 is a graphic chart showing the change of concentration of photosensitizer with the passage of time in normal rabbits.

The above test results are plotted in FIG. 2 and FIG. 3.

What is claimed is:

1. A method for detecting cholesterol which is deposited in the bodies of mammals comprising administering to a host an effective amount of a photosensitizer of at least one member selected from the group consisting of tetrapyrrole carboxylic acids having at least one carboxyl group represented by the following general formula (I), corresponding di- or tetrahydropyrrole carboxylic acids, mono-, di- or polyamides of said tetrapyrrole carboxylic acids with amino-mono- or dicarboxylic acids, and salts of the above compounds; applying light of sufficient wavelength to the area of said mammal to be examined in order to cause fluorescence of said photosensitizer; and observing the fluorescence emitted from the area in which cholesterol is deposited:

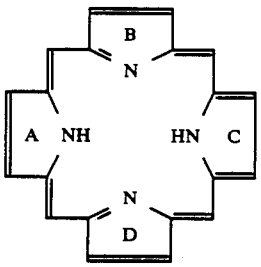

wherein
R₁ is methyl,

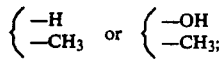

R₂ is H, vinyl, ethyl,

−CHCH₃,
 |
 OH acetyl,

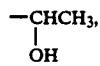

CH₂CH₂CO₂H or =CHCHO;
R₃ is methyl,

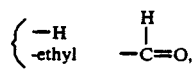

R₄ is H, vinyl, ethyl,

−CHCH₃,
 |
 OH
CH₂CH₂CO₂H =CHCHO or

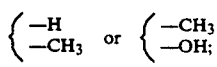

R₅ is methyl;
R₆ is H, CH₂CH₂CO₂H, CH₂CH₂CO₂R or CO₂H;
R₇ is CH₂CH₂CO₂H, CH₂CH₂CO₂R or

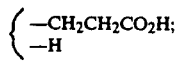

R₈ is methyl or

R₉ is H, COOH, CH₂COOH or methyl; provided that when R₁, R₂, R₃, R₄, R₇ and R₈ represents two substituents or are divalent and attached to the same carbon, the respective pyrrole ring to which attached is a dihydropyrrole;
R is lower alkyl or benzyl;
R₆ and R₉, taken together are

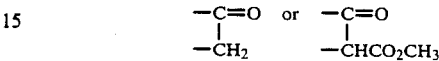

with the proviso that at least one of R₁–R₉ is a free carboxyl group.

2. The method for detecting cholesterol as claimed in claim 1, wherein said area of mammal to be examined is the intima of said mammal.

3. The method for detecting cholesterol as claimed in claim 1, wherein said amino-mono- or dicarboxylic acid is a natural α-amino-mono- or dicarboxylic acid.

4. The method for detecting cholesterol as claimed in claim 1, wherein said tetrapyrrole carboxylic acids have at least three carboxyl groups.

5. The method for detecting cholesterol as claimed in claim 4, wherein said tetrapyrrole carboxylic acids are represented by the following general formula:

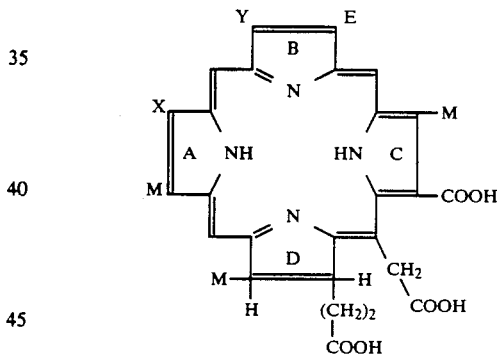

wherein;
X is H, vinyl, ethyl, acetyl or formyl;
Y is methyl or formyl;
M is methyl; and
E is ethyl.

6. The method for detecting cholesterol as claimed in claim 1, wherein said tetrapyrrol is di- or tetrahydro type.

7. The method for detecting cholesterol as claimed in claim 3, wherein said natural α-amino-mono- or dicarboxylic acid is one member selected from the group consisting of serine, alanine, glycine, aspartic acid and glutamic acid.

8. The method for detecting cholesterol as claimed in claim 1, wherein said photosensitizer is a chlorin derivative.

9. The method for detecting cholesterol as claimed in claim 7, wherein said amide is mono-L-aspartyl chlorin e₆ or mono-L-serinyl chlorin e₆.

* * * * *

UNITED STATES PATENT AND TRADEMARK OFFICE
CERTIFICATE OF CORRECTION

PATENT NO. : 4,997,639

DATED : March 5, 1991

INVENTOR(S) : Katsuo Aizawa, et al.

It is certified that error appears in the above-identified patent and that said Letters Patent is hereby corrected as shown below:

Column 1, line 53: "trademark supplied" should read as --trademark, supplied--

Column 3, line 50: "acids The" should read as --acids. The--

Column 3, line 56: "acid)" should read as --acid),--

Column 6, line 20: "ethyl" should read as --ethyl.--

Column 10, line 40: "$e_{66}$" should read as --$e_6$--

Column 11, lines 9 & 39: "Derivatives" should read as --Derivatives:--

Column 12, lines 16 & 45: "Derivatives" should read as --Derivatives:--

Column 16, line 52: "Derivatives" should read as --Derivatives:--

Column 17, lines 14 & 26: "Derivatives" should read as --Derivatives:--

Column 18, line 43: before "were" insert --which--

Column 18, line 62: "solution From" should read as --solution. From--

UNITED STATES PATENT AND TRADEMARK OFFICE
CERTIFICATE OF CORRECTION

PATENT NO. : 4,997,639

DATED : March 5, 1991

INVENTOR(S) : Katsuo Aizawa, et al.

It is certified that error appears in the above-identified patent and that said Letters Patent is hereby corrected as shown below:

Column 19, line 37: "70° C." should read as --70° C--

Column 19, line 64: "added then" should read as --added, then--

Column 20, line 54: "channel The" should read as --channel. The--

Column 21, line 29: "A dose 0.5" should begin a new paragraph.

Column 21, line 46: "observed When" should read as --observed. When--

Column 21, line 48: "beam no" should read as --beam, no--

Column 23, line 30: "$e_6$in" should read as --$e_6$ in--

Column 24, lines 31-32: delete "and 1 mg/kg of"

Signed and Sealed this

Seventeenth Day of November, 1992

*Attest:*

DOUGLAS B. COMER

*Attesting Officer*  *Acting Commissioner of Patents and Trademarks*